United States Patent [19]

Huffman et al.

[11] Patent Number: 4,577,035

[45] Date of Patent: Mar. 18, 1986

[54] 2,2'-ISOPROPYLIDINE BIS(TETRAHYDROFURAN)

[76] Inventors: George W. Huffman, 6502 Vermont Trail, Crystal Lake, Ill. 60014; William J. Pentz, 61 Margaret Ter.; David E. Vietti, 720 Millwood, both of Cary, Ill. 60013; Joseph P. Wuskell, 11 Lowell Rd., West Hartford, Conn. 06119

[21] Appl. No.: 675,710

[22] Filed: Nov. 28, 1984

[51] Int. Cl.$^4$ .......................................... C07D 307/12
[52] U.S. Cl. ................................... 549/472; 523/456
[58] Field of Search ........................................ 549/472

[56] References Cited

U.S. PATENT DOCUMENTS

| 2,681,917 | 6/1954 | Fauque et al. | 549/472 |
| 4,429,090 | 1/1984 | Hall | 526/177 |
| 4,429,091 | 1/1984 | Hall | 526/181 |
| 4,496,751 | 1/1985 | Still et al. | 549/472 |

FOREIGN PATENT DOCUMENTS

| 230447 | 1/1959 | Australia. |
| 588377 | 5/1947 | United Kingdom. |
| 190906 | 1/1967 | U.S.S.R. |

OTHER PUBLICATIONS

Karakhanov et al., Chemical Abstracts, vol. 98, (1982) 71847r.

Micovic et al., Chemical Abstracts, vol. 70, (1969), 106303m.

*Primary Examiner*—Richard L. Raymond
*Attorney, Agent, or Firm*—Neuman, Williams, Anderson & Olson

[57] ABSTRACT

The new composition of matter, 2,2'-isopropylidine bis(tetrahydrofuran) and method of preparation.

1 Claim, No Drawings

2,2'-ISOPROPYLIDINE BIS(TETRAHYDROFURAN)

This invention relates to a new composition of matter.

The new composition of matter in accordance with this invention is 2,2'-isopropylidine bis(tetrahydrofuran) having the following formula:

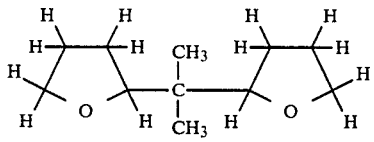

The above new composition of matter is produced in substantially quantitative yields by reacting furan and acetone to form isopropylidine difuran which is then hydrogenated using precious metal catalysts selected from platinum, palladium and rhodium.

The following examples illustrate the synthesis of the new composition of matter.

EXAMPLE 1

Preparation of 2,2'-Isopropylidine Difuran and Oligomers Thereof

Furan (1360 grams, 20 moles) was added to 1200 milliliters of 7M hydrochloric acid in a 5 liter 3-neck flask equipped with a stirrer, thermometer and addition funnel. Acetone (580 grams, 10 moles) was added slowly over 5 hours with vigorous stirring. The temperature was kept below 30° C. by the rate of addition of acetone or external cooling when necessary. The mixture was stirred vigorously overnight, the water layer was separated and the organic layer washed with 500 milliliters of 5% sodium bicarbonate, 500 milliliters of water and dried over anhydrous sodium sulfate. The unreacted furan and acetone were distilled off on a rotary evaporator under reduced pressure to give 1175 grams of orange liquid.

Analysis of the product by gas chromatography on a 6 foot column of carbowax C 20M on chromasorb WHP indicated that the product was a mixture of 2,2'-isopropylidine difuran (86% by weight) and oligomers A (10.5% by weight), B (0.08% by weight) and C. Pure 2,2'-isopropylidine difuran obtained by fractional distillation analyses: bp 124°–125° C., 78 mm; NMR (CDCl$_3$) δ7.26 (m, 2H) 6.26 (m, 2H), 6.00 (m, 2H) 1.66 (s, 6H).

2,2'-Isopropylidine difuran has the formula:

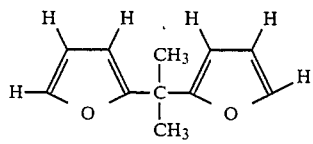

Oligomers A and B have the formula below and can be hydrogenated to give corresponding tetrahydro compounds.

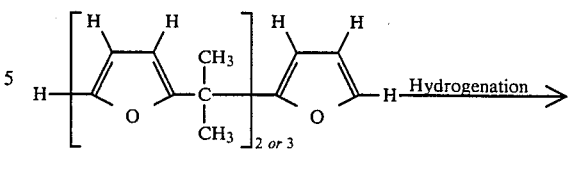

Oligomer C is a cyclic compound represented by the formula:

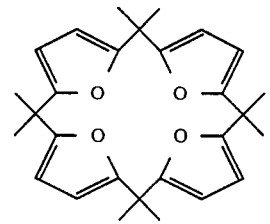

EXAMPLE 2

Methanol (800 milliliters) was added to a slurry of 10 grams of 5% palladium on carbon catalyst in 1000 grams of the product mixture as obtained in Example 1. The mixture was placed in a Parr one gallon stainless steel reactor and hydrogenated for four hours at 60°–80° C. and 400–800 psig hydrogen. When uptake of hydrogen ceased, the reactor was cooled, depressurized, and flushed with nitrogen. The catalyst was filtered off and the solvent removed under reduced pressure to give 1011 grams of nearly colorless liquid. The product was analyzed by gas-liquid chromatography and found to contain less than 0.2% of either 2,2'-isopropylidine difuran or oligomer A or oligomer B, these having been converted to the corresponding hydrogenated products (i.e., 2,2'-isopropylidine bis(tetrahydrofuran), A' and B'. The hydrogenated products were evident as a mixture of stereoisomers with longer retention times than the starting materials. The infrared and nuclear magnetic resonance spectra of this product mixture were nearly identical with that of pure 2,2'-isopropylidine bis(tetrahydrofuran) which was obtained by distillation of the product from a small amount of sodium hydroxide: bp 145°–146° C., 58 mm; IR 1070 cm$^{-1}$ (ether); NMR δ3.5–4.0 (m, 6H) 1.5–2.0 (m, 8H), 0.73, 0.9 (s, 6H, CH$_3$, isomers).

EXAMPLE 3

Substantially pure 2,2'-isopropylidine difuran (50 grams), isopropanol (50 grams) and 2.5 grams of 5% palladium on carbon catalyst were placed in a 600 milliliter Parr autoclave and hydrogenated for 3 hours at 60° C. and a constant hydrogen pressure of 100 psig. 2,2'-Isopropylidine bis(tetrahydrofuran) was produced in nearly quantitative yield.

EXAMPLE 4

The hydrogenation as described in Example 3 was repeated except 2.5 grams of 5% rhodium on carbon catalyst was used. The product, 2,2'-isopropylidine bis(tetrahydrofuran), was obtained in nearly quantitative yield.

The 2,2'-isopropylidine bis(tetrahydrofuran) of the present invention is useful in epoxy resins. More particularly, it is useful as a reactive diluent in epoxy resins to lower the epoxy resin viscosity and can be used to modify epoxy resins in lieu of the furan compounds as disclosed, for example, in U.S. Pat. Nos. 3,072,606 and 3,072,607. Mixtures of 2,2'-isopropylidine bis(tetrahydrofuran) and hydrogenated oligomers A' and B' can be used as additives in sulfur compositions such as are used for producing vehicle tires.

Those modifications and equivalents which fall within the spirit of the invention are to be considered a part thereof.

What is claimed is:

1. The composition of matter 2,2'-isopropylidine bis(tetrahydrofuran).

* * * * *